United States Patent
Lee et al.

(10) Patent No.: US 11,248,059 B2
(45) Date of Patent: Feb. 15, 2022

(54) ANTIBODY HAVING IMPROVED STABILITY AND SPECIFICALLY BINDING TO HER2

(71) Applicant: ABCLON INC., Seoul (KR)

(72) Inventors: Jong Seo Lee, Gyeonggi-do (KR); Kyu Tae Kim, Gyeonggi-Do (KR); Young Ha Lee, Seoul (KR); In Sik Hwang, Incheon (KR); Bong Kook Ko, Seoul (KR)

(73) Assignee: ABCLON INC., Seoul (KR)

( * ) Notice: Subject to any disclaimer, the term of this patent is extended or adjusted under 35 U.S.C. 154(b) by 442 days.

(21) Appl. No.: 16/093,486

(22) PCT Filed: Apr. 12, 2017

(86) PCT No.: PCT/KR2017/003827
§ 371 (c)(1),
(2) Date: Oct. 12, 2018

(87) PCT Pub. No.: WO2017/179862
PCT Pub. Date: Oct. 19, 2017

(65) Prior Publication Data
US 2019/0153118 A1    May 23, 2019

(30) Foreign Application Priority Data
Apr. 12, 2016  (KR) ........................ 10-2016-0044747

(51) Int. Cl.
| C07K 16/30 | (2006.01) |
| C07K 16/28 | (2006.01) |
| A61P 35/00 | (2006.01) |
| C07K 16/32 | (2006.01) |
| A61K 39/00 | (2006.01) |
| G01N 33/574 | (2006.01) |
| A61K 39/395 | (2006.01) |
| A61P 43/00 | (2006.01) |

(52) U.S. Cl.
CPC .............. *C07K 16/32* (2013.01); *A61K 39/00* (2013.01); *A61K 39/395* (2013.01); *A61P 35/00* (2018.01); *A61P 43/00* (2018.01); *G01N 33/574* (2013.01); *C07K 2317/24* (2013.01); *C07K 2317/56* (2013.01); *C07K 2317/565* (2013.01); *C07K 2317/73* (2013.01)

(58) Field of Classification Search
CPC ..................................................... C07K 16/30
See application file for complete search history.

(56) References Cited

U.S. PATENT DOCUMENTS

| 5,821,337 A | 10/1998 | Carter et al. |
| 8,609,095 B2 | 12/2013 | Pedersen et al. |
| 2004/0213791 A1* | 10/2004 | Bander .............. A61K 47/6869 424/155.1 |
| 2007/0059806 A1* | 3/2007 | Arnon .............. G01N 33/56983 435/91.1 |
| 2010/0047230 A1 | 2/2010 | Mamalaki et al. |

FOREIGN PATENT DOCUMENTS

| CN | 1487996 A | 4/2004 |
| CN | 103833854 A | 6/2014 |
| CN | 105164160 A | 12/2015 |
| KR | 10-2003-0074634 A | 9/2003 |
| KR | 101453462 B1 | 10/2014 |
| WO | WO-2008/031531 A1 | 3/2008 |
| WO | WO-2010/047509 A2 | 4/2010 |
| WO | WO-2014/185704 A1 | 11/2014 |
| WO | WO-2015-074528 A1 | 5/2015 |

OTHER PUBLICATIONS

Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Extended European Search Report from corresponding European Patent Application No. EP 17782617.9 dated Mar. 26, 2019.
Office Action from corresponding Japanese Patent Application No. 2018-554349, dated Sep. 3, 2019.
Ko, Bong-Kook, et al.; "Affinity Maturation of Monoclonal Antibody 1E11 by Targeted Randomization in CDR3 Regions Optimizes Therapeutic Antibody Targeting of HER2-Positive Gastric Cancer", PLOS ONE, Jul. 30, 2015, pp. 1-16.
Akiyama T, et al. (1986) "The Product of the Human c-erbB-2 Gene: A 185-Kilodalton Glycoprotein with Tyrosine Kinase Activity." *Science*, 232(4758):1644-1646.
Bussolati, G, et al. (2005) "A modified Trastuzumab antibody for the immunohistochemical detection of HER-2 overexpression in breast cancer." *British Journal of Cancer*, 92:1261-1267.
Correia, IR., (2010) "Stability of IgG isotypes in serum." *MAbs*, 2(3):221-232 (e30295).
Diepold, K., et al. (2012) "Simultaneous Assessment of Asp Isomerization and Asn Deamidation in Recombinant Antibodies by LC-MS following Incubation at Elevated Temperatures." *PLos One*, 7(1).

(Continued)

*Primary Examiner* — Michael Allen
(74) *Attorney, Agent, or Firm* — Harness, Dickey & Pierce, P.L.C.

(57) ABSTRACT

The present invention replaces an amino acid residue of a specific region of a parent antibody so as to improve the stability of the antibody, thereby improving druggability. A variant antibody of the present invention, compared to a parent antibody hz1E11, has significantly improved stability while having nearly the same productivity and efficacy. Therefore, the variant antibody of the present invention exhibits, in the development of HER2-specific antibodies, excellent characteristics such as reduction in production costs, inhibition of efficacy reduction and reduction of side effects.

4 Claims, 3 Drawing Sheets

Specification includes a Sequence Listing.

(56) References Cited

OTHER PUBLICATIONS

Glazyrin A, et al. (2007) "Direct Detection of Herceptin/Trastuzumab Binding on Breast Tissue Sections." *J Histology & Cytochemistry*, 55(1):25-33.

Sapino, A., et al. (2007) "Patients with advanced stage breast carcinoma immunoreactive to biotinylated Herceptin® are most likely to benefit from trastuzumab-based therapy: an hypothesis-generating study." *Annals of Oncology*, 18:1963-1968.

Uhlman and Peyman (1990) "Antisense Oligonucleotides: A New Therapeutic Principle." Chemical Reviews, 90(4):543-584.

International Search Report (ISR) from corresponding International Patent Application No. PCT/KR2017/003827, dated Jul. 10, 2017, with an English translation.

Office Action from corresponding Chinese Patent Application No. 201780023274.4, dated May 18, 2021.

Chen, Mil Med Sci, vol. 38, No. 5, May 2014.

\* cited by examiner

```
                         SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: CDRH1 of hz1E11 antibody

<400> SEQUENCE: 1

Ser Tyr Thr Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of hz1E11 antibody

<400> SEQUENCE: 2

Tyr Ile Ser Asn Gly Gly Gly Ser Thr Tyr Tyr Pro Asp Thr Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDRH3 of hz1E11 antibody

<400> SEQUENCE: 3

His Leu Gly Gly Thr Ala Ser Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDRL1 of hz1E11 antibody

<400> SEQUENCE: 4

Leu Ala Ser Gln Thr Ile Gly Thr Trp Leu Ala
1               5                   10

<210> SEQ ID NO 5
<211> LENGTH: 6
<212> TYPE: PRT
<213> ORGANISM: Artificial Sequence
<220> FEATURE:
<223> OTHER INFORMATION: CDRL2 of hz1E11 antibody

<400> SEQUENCE: 5

Ala Thr Ser Leu Ala Asp
1               5
```

<210> SEQ ID NO 6
<211> LENGTH: 9
<212> TYPE: PRT
<213> ORGANISM: Artificial Sequence
<220> FEATURE:
<223> OTHER INFORMATION: CDRL3 of hz1E11 antibody

<400> SEQUENCE: 6

Gln Gln Leu Tyr Ser Thr Pro Trp Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Amino acid sequence of hz1E11 heavy chain
      variable region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Asn Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Gly Gly Thr Ala Ser Phe Asp Tyr Trp Gly Gln Gly
            100                 105                 110

Thr Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Amino acid sequence of hz1E11 light chain
      variable region

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Trp
                85                  90                  95

Thr Phe Gly Gln Gly Thr Lys Val Glu Ile Lys
            100                 105

```
<210> SEQ ID NO 9
<211> LENGTH: 17
<212> TYPE: PRT
<213> ORGANISM: Artificial Sequence
<220> FEATURE:
<223> OTHER INFORMATION: CDRH2 of hz1E11.10

<400> SEQUENCE: 9

Tyr Ile Ser Ala Gly Gly Ser Thr Tyr Tyr Pro Asp Thr Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: CDRH2 of hz1E11.20

<400> SEQUENCE: 10

Tyr Ile Ser Asn Ala Gly Gly Ser Thr Tyr Tyr Pro Asp Thr Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: CDRH2 of hz1E11.10/20

<400> SEQUENCE: 11

Tyr Ile Ser Ala Ala Gly Gly Ser Thr Tyr Tyr Pro Asp Thr Val Lys
1               5                   10                  15

Gly

<210> SEQ ID NO 12
<211> LENGTH: 107
<212> TYPE: PRT
<213> ORGANISM: Artificial Sequence
<220> FEATURE:
<223> OTHER INFORMATION: Amino acid sequence of hz1E11.01 light chain
      variable region

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Trp
                85                  90                  95

Thr Phe Gly Gln Gly Thr Lys Val Glu Ile Lys
            100                 105
```

<210> SEQ ID NO 13
<211> LENGTH: 107
<212> TYPE: PRT
<213> ORGANISM: Artificial Sequence
<220> FEATURE:
<223> OTHER INFORMATION: Amino acid sequence of hz1E11.02 light chain variable region

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Ala Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Trp
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Amino acid sequence of hz1E11.01/02 light chain variable region

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Ala Ala Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Trp
                85                  90                  95

Thr Phe Gly Gln Gly Thr Lys Val Glu Ile Lys
            100                 105

<210> SEQ ID NO 15
<211> LENGTH: 32
<212> TYPE: DNA
<213> ORGANISM: Artificial Sequence
<220> FEATURE:
<223> OTHER INFORMATION: F_N52aA primer

<400> SEQUENCE: 15
gtagcctaca tctccgccgg gggcggaagt ac                                    32

<210> SEQ ID NO 16
<211> LENGTH: 32
<212> TYPE: DNA

```
<213> ORGANISM: Artificial Sequence
<220> FEATURE:
<223> OTHER INFORMATION: R_N52aA primer

<400> SEQUENCE: 16
gtacttccgc ccccggcgga gatgtaggct ac                          32

<210> SEQ ID NO 17
<211> LENGTH: 30
<212> TYPE: DNA
<213> ORGANISM: Artificial Sequence
<220> FEATURE:
<223> OTHER INFORMATION: F_G53A primer

<400> SEQUENCE: 17
ctacatctcc aacgccggcg gaagtacgta                             30

<210> SEQ ID NO 18
<211> LENGTH: 30
<212> TYPE: DNA
<213> ORGANISM: Artificial Sequence
<220> FEATURE:
<223> OTHER INFORMATION: R_G53A primer

<400> SEQUENCE: 18
tacgtacttc cgccggcgtt ggagatgtag                             30

<210> SEQ ID NO 19
<211> LENGTH: 33
<212> TYPE: DNA
<213> ORGANISM: Artificial Sequence
<220> FEATURE:
<223> OTHER INFORMATION: F_D56A primer

<400> SEQUENCE: 19
gcaacgagtc tcgctgccgg tgtgccttcc aga                         33

<210> SEQ ID NO 20
<211> LENGTH: 33
<212> TYPE: DNA
<213> ORGANISM: Artificial Sequence
<220> FEATURE:
<223> OTHER INFORMATION: R_D56A primer

<400> SEQUENCE: 20
tctggaaggc acaccggcag cgagactcgt tgc                         33

<210> SEQ ID NO 21
<211> LENGTH: 32
<212> TYPE: DNA
<213> ORGANISM: Artificial Sequence
<220> FEATURE:
<223> OTHER INFORMATION: F_G57A primer

<400> SEQUENCE: 21
cgagtctcgc tgacgccgtg ccttccagat tt                          32

<210> SEQ ID NO 22
<211> LENGTH: 32
<212> TYPE: DNA
<213> ORGANISM: Artificial Sequence
<220> FEATURE:
<223> OTHER INFORMATION: R_G57A primer

<400> SEQUENCE: 22
aaatctggaa ggcacggcgt cagcgagact cg                          32
```

```
<210> SEQ ID NO 23
<211> LENGTH: 6
<212> TYPE: PRT
<213> ORGANISM: Artificial Sequence
<220> FEATURE:
<223> OTHER INFORMATION: hexahistidine

<400> SEQUENCE: 23

His His His His His His
1               5
```

ANTIBODY HAVING IMPROVED STABILITY AND SPECIFICALLY BINDING TO HER2

CROSS-REFERENCE TO RELATED APPLICATIONS

This application is a national phase application of PCT Application No. PCT/KR2017/003827, filed on Apr. 12, 2017, which claims the benefit and priority to Korean Patent Application No. 10-2016-0044747, filed Apr. 12, 2016. The entire disclosures of the applications identified in this paragraph are incorporated herein by references.

FIELD

The present invention relates to a human epidermal growth factor receptor 2 (HER2) antibody with improved stability used in the prevention or treatment of HER2-related diseases, especially, cancer.

BACKGROUND

The HER2/neu(ErbB2) gene encodes 185 kDa transmembrane glycoprotein that belongs to the family of epidermal growth factor receptors (EGFR). The HER2 protein consists of a 620 aa extracellular domain, followed by a 23 aa transmembrane domain, and a 490 aa intracellular domain with a tyrosine kinase activity (Akiyama T, et al., Science, 232(4758):1644-1646 (1986)).

HER2 antibodies with various characteristics are reported in a number of documents, and one of the most commercially successful antibodies of these HER2 antibodies is a trastuzumab antibody (commercialized as Herceptin™, U.S. Pat. No. 5,821,337) (Sapino, A., et al., Annals of Oncology (2007) 18: 1963-1968; Bussolati, G, et al., British Journal of Cancer (2005) 92, 1261-1267; and Glazyrin A, et al., J Histology & Cytochemistry (2007) 55(1):25-33).

Even though the trastuzumab antibody has been commercially successful, this antibody shows an effect thereof in only some of HER2 expressed patients. Therefore, there have been attempts to improve prognosis of cancer patients, who are non-responsive or poor-responsive to trastuzumab through co-administration with trastuzumab. For instance, WO 2008/031531 discloses that the co-administration of trastuzumab and pertuzumab, which bind to the same target, HER2, suppresses cancer metastasis, and WO 2014/185704 discloses that the co-administration of trastuzumab with hz1E11, which binds to different epitope of HER2, exhibits anticancer activity.

The improvement in stability of therapeutic antibodies can increase comprehensive efficiency, such as reduction of costs, increase of efficacy, and reduction of side effects. Hence, research to secure antibodies with improved stability through modification in the sequences of therapeutic antibodies is being conducted ((WO 2010/047509; Diepold, K., et al., PLos One (2012) 7(1): e30295; Correia, I R., MAbs (2010) 2(3): 221-232).

Throughout the specification, many papers and patent documents are used as references, and the citations thereof are represented. The disclosure of the cited papers and patent documents is incorporated in the present specification by reference in its entirety, to describe a level of the technical field to which the present invention pertains and content of the present invention more clearly.

SUMMARY

Technical Problem

The present inventors endeavored to improve structural stability of hz1E11 (see Korean Patent No. 1453462), which is the antibody that had already been developed by the present inventors. The structural stability of antibodies is an important consideration in the commercial development of medicines, and the bad structural stability causes problems, such as the deterioration in quality control, the reduction in efficacy, and the increase in side effects. The present inventors discovered four amino acid resides that may have a great effect on stability among amino acid resides at various positions of hz1E11, and then manufactured variants with substituents of these amino acid residues, and thus completed hz1E11 variants that have improved stability and similar productivity and efficacy to the mother antibody.

Therefore, an aspect of the present invention is to provide an antibody to human epidermal growth factor receptor 2 (HER2), the antibody with improved stability, or an antigen binding fragment thereof Another aspect of the present invention is to provide a nucleic acid molecule encoding an antibody to HER2, the antibody with improved stability, or an antigen binding fragment thereof.

Still another aspect of the present invention is to provide a recombinant vector comprising the nucleic acid molecule.

Still another aspect of the present invention is to provide a host cell transformed with the recombinant vector.

Still another aspect of the present invention is to provide a pharmaceutical composition for the prevention or treatment of cancer.

Still another aspect of the present invention is to provide a method for the prevention or treatment of cancer, the method comprising administering, to a subject, the pharmaceutical composition for the prevention or treatment of cancer.

Still another aspect of the present invention is to provide a kit for the diagnosis of cancer.

Other purposes and advantages of the present disclosure will become more obvious with the following detailed description of the invention, claims, and drawings.

Technical Solution

In accordance with an aspect of the present invention, there is provided an antibody to human epidermal growth factor receptor 2 (HER2) or an antigen binding fragment thereof, the antibody with improved stability, the antibody comprising: (a) a heavy chain variable region comprising (i) complementarity determining region (CDR) H1 of SEQ ID NO: 1, (ii) CDRH2 of SEQ ID NO: 2, and (iii) CDRH3 of SEQ ID NO: 3, wherein at least one of the 4th and 5th amino acid residues in SEQ ID NO: 2 is substitution modified with another amino acid; and (b) a light chain variable region comprising CDRL1 of SEQ ID NO: 4, CDRL2 of SEQ ID NO: 5, and CDRL3 of SEQ ID NO: 6.

The present inventors endeavored to improve structural stability of hz1E11 (see Korean Patent No. 1453462), which is the antibody that had already been developed by the present inventors. The structural stability of antibodies is an important consideration in the commercial development of medicines, and the bad structural stability causes problems, such as the deterioration in quality control, the reduction in efficacy, and the increase in side effects. The present inventors discovered four amino acid resides that may have a great effect on stability among amino acid resides at various positions of hz1E11, and then manufactured variants with substituents of these amino acid residues, and thus completed hz1E11 variants that have improved stability and similar productivity and efficacy to the mother antibody.

Among the four amino acid residues established by the present inventors, two amino acid residues are located in CDRH2 of the heavy chain variable region. Specifically, the 4th and 5th amino acid residues in CDRH2 of SEQ ID NO: 2 have an effect on structural stability. The substitution of at least one of the two amino acids with another amino acid leads to improved stability while the productivity and efficacy of the mother antibody are maintained.

According to the present invention, Asn, which is the 4th amino acid residue in CDRH2, can be substituted with any other amino acid.

According to an embodiment of the present invention, the 4th amino acid residue in SEQ ID NO: 2 of CDRH2 is substituted with Ala, Gly, Cys, Ile, Leu, Met, Phe, Trp, or Val, more specifically Ala, Gly, Ile, Leu, or Val, still more specifically Ala or Gly, and most specifically Ala.

According to the present invention, Gly, which is the 5th amino acid residue in CDRH2, can be substituted with any other amino acid.

According to an embodiment of the present invention, the 5th amino acid residue in SEQ ID NO: 2 of CDRH2 is substituted with Ala, Cys, Ile, Leu, Met, Phe, Trp, or Val, more specifically Ala, Ile, Leu, or Val, still more specifically Ala or Val, and most specifically Ala.

The amino acid substitution scheme adopted in the present invention is that, while an original amino acid is substituted with another amino acid, the substituted amino acid is selected to have an R group with as low reactivity as possible and be structurally small and stable.

According to an embodiment of the present invention, the CDRH2 of SEQ ID NO: 2 with substitution modification includes an amino acid sequence of SEQ ID NO: 9, an amino acid sequence of SEQ ID NO: 10, or an amino acid sequence of SEQ ID NO: 11.

According to an embodiment of the present invention, the modified antibody of the present invention have improved stability by applying a modification to a light chain variable region besides the heavy chain variable region. Specifically, the variable region of the antibody of the present invention contains an amino acid sequence of SEQ ID NO: 12, SEQ ID NO: 13, or SEQ ID NO: 14.

In accordance with an aspect of the present invention, there is provided an antibody to human epidermal growth factor receptor 2 (HER2) or an antigen binding fragment thereof, the antibody with improved stability, the antibody comprising: (a) a heavy chain variable region comprising (i) complementarity determining region (CDR) H1 of SEQ ID NO: 1, (ii) CDRH2 of SEQ ID NO: 2, and (iii) CDRH3 of SEQ ID NO: 3; and (b) a light chain variable region comprising SEQ ID NO: 8, wherein at least one of the 56th and 57th amino acid residues in SEQ ID NO: 8 is substitution-modified with another amino acid.

Among the four amino acid residues established by the present inventors, two amino acid residues may be located in a framework region but not CDR of the light chain variable region. Specifically, the 56th and 57th amino acid residues in SEQ ID NO: 8 have an effect on structural stability. The substitution of at least one of the two amino acids with another amino acid leads to improved stability while the productivity and efficacy of a mother antibody are maintained.

According to the present invention, Asp, which is the 56th amino acid residue in SEQ ID NO: 8, can be substituted with any other amino acid.

According to an embodiment of the present invention, the 56th amino acid residue in SEQ ID NO: 8 is substituted with Ala, Gly, Cys, Ile, Leu, Met, Phe, Trp, or Val, more specifically Ala, Gly, Ile, Leu, or Val, still more specifically Ala or Gly, and most specifically Ala.

According to the present invention, Gly, which is the 57th amino acid residue in SEQ ID NO: 8, can be substituted with any other amino acid.

According to an embodiment of the present invention, the 57th amino acid residue in SEQ ID NO: 8 is substituted with Ala, Cys, Ile, Leu, Met, Phe, Trp, or Val, more specifically Ala, Ile, Leu, or Val, still more specifically Ala or Val, and most specifically Ala.

According to an embodiment of the present invention, the amino acid sequence of SEQ ID NO: 8 with substitution modification includes an amino acid sequence of SEQ ID NO: 12, an amino acid sequence of SEQ ID NO: 13, or an amino acid sequence of SEQ ID NO: 14.

The antibody of the present invention has excellent cell killing ability or proliferation inhibiting ability on various VEGFR2-expressing cancer cells. As used herein, the terms "cell killing" and "proliferation inhibiting" used while citing cancer cells is used in mixture with the same meaning.

As used herein, the term "antibody" refers to a specific antibody to HER2, and includes not only the whole antibody form but also an antigen binding fragment of an antibody molecule.

The whole antibody has a structure having two full-length light chains and two full-length heavy chains, and the light chains are linked with the heavy chains via disulfide bonds, respectively. A heavy chain constant region has gamma ($\gamma$), mu ($\mu$), alpha ($\alpha$), delta ($\delta$), and epsilon ($\epsilon$) types, and gamma1 ($\gamma$1), gamma2 ($\gamma$2), gamma3 ($\gamma$3), gamma4 ($\gamma$4), alpha1 ($\alpha$1), and alpha2 ($\alpha$2) subclasses. A light chain constant region has kappa ($\kappa$) and lambda ($\lambda$) types (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, sinauer Associates, Inc., Sunderland, Mass. (1984)).

As used herein, the term "antigen binding fragment" refers to a fragment that retains an antigen binding function, and includes Fab, F(ab'), F(ab')$_2$, Fv, and the like. Of the antibody fragments, Fab has a structure of having heavy chain and light chain variable regions, a light chain constant region, and a first heavy chain constant region ($C_{H1}$), and Fab has one antigen binding site. Fab' is different from Fab in that Fab' has a hinge region comprising one or more cysteine residues at the C-terminus of the heavy chain $C_{H1}$ domain. F(ab')$_2$ antibody is generated through a disulfide bond formed between the cysteine residues in the hinge regions of Fab' fragments. Fv is a minimal antibody segment having only a heavy chain variable domain and a light chain variable domain, and a recombinant technique that produces an Fv fragment is disclosed in WO 88/10649, WO 88/106630, WO 88/07085, WO 88/07086, and WO 88/09344. A two-chain Fv has a structure in which a heavy chain variable region and a light chain variable region are linked through a non-covalent linkage, and a single-chain Fv includes a heavy chain variable region and a light chain variable region covalently linked to each other via a peptide linker or directly linked at the C-terminus, thereby forming a dimeric structure as in the two-chain Fv. These antibody fragments may be obtained using proteases (for example, the whole antibody is restriction digested with papain to obtain Fab fragments, and is restriction digested with pepsin to obtain F(ab')2 fragments), and may be fabricated by a genetic recombinant technique.

The antibody of the present invention is a form of Fab or the whole antibody. In addition, the heavy chain constant region may be selected from any one isotype of gamma (γ), mu (μ), alpha (α), delta (δ), and epsilon (ε) types. Preferably, the constant region includes gamma 1 (IgGI), gamma 3 (IgG3), and gamma 4 (IgG4) isotypes, and most preferably the constant region is gamma 1 (IgGI) isotype. The light chain constant region may be κ or λ type, and may preferably be κ type. Therefore, a preferable antibody of the present invention may have Fab or IgG1 type having κ light chain and γ1 heavy chain.

As used herein, the term "heavy chain" refers to the full-length heavy chain and fragments thereof, the full-length heavy chain comprising a variable region domain $V_H$ that includes an amino acid sequence sufficient to provide specificity to an antigen, and three constant region domains, $C_{H1}$, $C_{H2}$, and $C_{H3}$. In addition, as used herein, the term "light chain" refers to the full-length light chain and fragments thereof, the full-length light chain comprising a variable domain $V_L$ that includes an amino acid sequence sufficient to impart specificity to an antigen, and a constant domain $C_L$.

As used herein, the term "complementarity determining region (CDR)" refers to an amino acid sequence of a hypervariable region of an immunoglobulin heavy chain or light chain (Kabat et al., Sequences of Proteins of Immunological Interest, 4th Ed., U.S. Department of Health and Human Services, National Institutes of Health (1987)). The heavy chain (CDRH1, CDRH2, and CDRH3) and the light chain (CDRL1, CDRL2, and CDRL3) each include three CDRs. CDRs provide major contact residues in the binding of an antibody to an antigen or epitope.

The antibody of the present invention includes monoclonal antibodies, multi-specific antibodies, human antibodies, humanized antibodies, chimeric antibodies, single-chain Fvs (scFVs), single-chain antibodies, Fab fragments, F(ab') fragments, disulfide-linked Fvs (sdFVs), and anti-idiotype (anti-Id) antibodies, and epitope-binding fragments of the antibodies, but is not limited thereto.

In accordance with still another aspect of the present invention, there is provided a nucleic acid molecule encoding the antibody to HER2 or the antigen binding fragment thereof of the present invention.

As used herein, the term "nucleic acid molecule" has a meaning comprehensively comprising DNA molecules (gDNA and cDNA) and RNA molecules, and a nucleotide as a basic constituent unit in the nucleic acid molecule includes natural occurring nucleotides, and analogues with modified sugars or bases (Scheit, Nucleotide Analogs, John Wiley, New York (1980); and Uhlman and Peyman, Chemical Reviews, 90:543-584 (1990)).

In accordance with another aspect of the present invention, there is provided a recombinant vector comprising the nucleic acid molecule of the present invention.

As used herein, the term "vector" refers to any vehicle that is used to express a target gene in a host cell, and includes: plasmid vectors; cosmid vectors; and viral vectors, such as bacteriophage vectors, adenoviral vectors, retroviral vectors, and adeno-associated viral vectors.

According to a preferable embodiment of the present invention, a nucleic acid molecule encoding a light chain variable region and a nucleic acid molecule encoding a heavy chain variable region are operatively linked with a promoter.

As used herein, the term "operatively linked" refers to a functional linkage between a nucleic acid expression control sequence (e.g., a promoter, a signal sequence, or an array of transcription regulation factor binding sites) and another nucleic acid sequence, by which the control sequence controls the transcription and/or translation of the another nucleic acid sequence.

The recombinant vector system of the present invention can be constructed by various methods known in the art, and a specific method thereof is disclosed in Sambrook et al., Molecular Cloning, A Laboratory Manual, Cold Spring Harbor Laboratory Press (2001), which is incorporated herein by reference.

The vector of the present invention may be typically constructed as a vector for cloning or a vector for expression. In addition, the vector of the present invention may be constructed by using a prokaryotic or eukaryotic cell as a host.

For example, in cases where the vector of the present invention is an expression vector and an eukaryotic cell is used as a host cell, a promoter derived from the genome of a mammalian cell (e.g., metallothionein promoter, β-actin promoter, human hemoglobin promoter, and human muscle creatine promoter) or a promoter derived from mammalian viruses (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of Moloney virus, Epstein-Barr virus (EBV), and Rous sarcoma virus (RSV)) may be used, and a polyadenylated sequence may be commonly used as the transcription termination sequence.

The vector of the present invention may be fused with the other sequences to facilitate the purification of the antibody expressed therefrom. Examples of the fusion sequence include, for example, glutathione S-transferase (Pharmacia, USA), maltose binding protein (NEB, USA), FLAG™ (IBI, USA), and 6×His (hexahistidine (SEQ ID NO: 23); QIAGEN™, USA).

Since the protein expressed by the vector of the present invention is an antibody, the expressed antibodies can be easily purified through protein A column or the like even without additional sequences for purification.

Meanwhile, the expression vector of the present invention includes, as a selective marker, an antibiotic agent-resistant gene that is ordinarily used in the art, and may include resistant genes against ampicillin, gentamycin, carbenicillin, chloramphenicol, streptomycin, kanamycin, geneticin, neomycin, and tetracycline.

In accordance with an aspect of the present invention, there is provided a host cell transformed with the recombinant vector.

As host cells capable of performing continuous cloning and expression while stabilizing the vector of the present invention, any host cell that is known in the art may be used, and for example, examples of eukaryotic host cells suitable for the vector may be monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293, but are not limited thereto.

In accordance with still another aspect of the present invention, there is provided a pharmaceutical composition for the prevention or treatment of cancer, the pharmaceutical composition comprising: (a) a pharmaceutical effective amount of the antibody to HER2 or antigen binding fragment thereof of the present invention; and (b) a pharmaceutically acceptable carrier.

In accordance with still another aspect of the present invention, there is provided a pharmaceutical composition for the prevention or treatment of cancer, the pharmaceutical composition comprising: the antibody to HER2 or antigen binding fragment thereof of the present invention; and a histidine-buffer containing 1-200 mM histidine.

According to an embodiment of the present invention, the concentration of histidine contained in the histidine-buffer may be 1-200 mM, more specifically 1-150 mM, 1-100 mM, 1-50 mM, 1-40 mM, 1-30 mM, or 1-20 mM, and most specifically 10 mM.

According to another embodiment of the present invention, the pH of the histidine-buffer may be 5-7, more specifically 5-6.5 or 5.5-6.5, and most specifically 6.

According to still another embodiment of the present invention, the histidine-buffer may contain 50-300 mM, more specifically 10-200 mM, 50-200 mM, or 100-200 mM, and most specifically 150 mM sodium chloride.

According to an embodiment of the present invention, the antibody to HER2 or antigen binding fragment thereof of the present invention shows significantly excellent stability even in stress conditions when stored in the histidine-buffer, compared with when stored in a PBS buffer. Therefore, the pharmaceutical composition containing a histidine-buffer for the prevention or treatment of cancer has an excellent effect in the improvement of stability of the pharmaceutical composition containing an antibody to HER2 or an antigen binding fragment thereof as an active ingredient.

Since the pharmaceutical composition of the present invention uses, as an active ingredient, the antibody to HER2 or antigen binding fragment thereof of the present invention, the overlapping descriptions therebetween are omitted to avoid excessive complication of the specification due to repetitive descriptions thereof.

As validated in the examples below, the antibody to HER2 of the present invention, when co-administered with trastuzumab, can kill cancer cells (especially, breast cancer cells, more specifically, HER2-expressing breast cancer cells) with significantly improved cell killing ability, and thus is very effective in the treatment of cancer (especially, breast cancer, more specifically, HER2-expressing breast cancer). According to an embodiment of the present invention, the pharmaceutical composition further contains a trastuzumab antibody.

The cancer that can be prevented or treated by the composition of the present invention includes various cancers known in the art, and examples thereof include breast cancer, ovarian cancer, stomach cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer, or ureteral cancer.

Specifically, the cancer that can be prevented or treated by the composition of the invention is HER2-expressing cancer, more specifically HER2-expressing breast cancer.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and agents are described in detail in Remington's Pharmaceutical Sciences (19th ed., 1995).

The pharmaceutical composition of the present invention may be administered parentally, for example, intravenous injection, subcutaneous injection, muscular injection, intraperitoneal injection, topical administration, intranasal administration, intrapulmonary administration, rectal administration, or the like.

The appropriate dose of the pharmaceutical composition of the present invention varies depending on factors, such as a formulating method, a manner of administration, patient's age, body weight, gender, morbidity, food, a time of administration, a route of administration, an excretion rate, and response sensitivity. An ordinarily skilled practitioner can easily determine and prescribe the dose that is effective for the desired treatment or prevention. According to a preferable embodiment of the present invention, the daily dose of the pharmaceutical composition of the present invention is 0.0001-100 mg/kg. As used herein, the term "pharmaceutically effective amount" refers to an amount sufficient to prevent or treat cancer.

The pharmaceutical composition of the present invention may be formulated into a unit dosage form or may be prepared in a multi-dose container by using a pharmaceutically acceptable carrier and/or excipient according to a method that is easily conducted by a person having an ordinary skill in the art to which the present invention pertains. Here, the dosage form may be a solution in an oily or aqueous medium, a suspension, an emulsion, an extract, a pulvis, a suppository, a powder, granules, a tablet, or a capsule, and may further include a dispersant or a stabilizer.

According to an embodiment of the present invention, the pharmaceutical composition of the present invention further contains a trastuzumab antibody. As used herein, the term "trastuzumab" refers to an antibody disclosed in U.S. Pat. No. 5,821,337.

In accordance with an aspect of the present invention, there is provided a method for the prevention or treatment of cancer, the method comprising administering, to a subject, a pharmaceutical composition comprising, as an active ingredient, the antibody to HER2 or antigen binding fragment thereof of the present invention.

As used herein, the term "administration" or "administer" refers to the direct application of a therapeutically effective amount of the composition of the present invention to a subject (individual) in need of the composition, thereby forming the same amount thereof in the body of the subject.

The term "therapeutically effective amount" of the composition refers to the content of the composition, which is sufficient to provide a therapeutic or prophylactic effect to a subject, to which the composition is to be administered, and thus the term has a meaning encompassing "prophylactically effective amount". As used herein, the term "subject" includes, but is not limited to, a human being, mouse, rat, guinea pig, dog, cat, horse, cow, pig, monkey, chimpanzee, baboon, or rhesus monkey. Specifically, the subject of the present invention is a human being.

Since the method for the prevention or treatment of cancer in the present invention includes a step of administering the pharmaceutical composition for prevention or treatment of cancer according to an aspect of the present invention, the overlapping descriptions therebetween are omitted to avoid excessive complication of the specification.

The above-described antibody to HER2 or antigen biding fragment thereof can be used for diagnosis, for example, diagnosis of cancer.

In accordance with still another aspect of the present invention, there is provided a kit for the diagnosis of cancer, the kit comprising the antibody to HER2 or antigen binding fragment thereof of the present invention.

Since the diagnostic kit of the present invention includes the above-described antibody to HER2 or antigen binding fragment thereof of the present invention and is used to diagnose the same disease as the pharmaceutical composition of the present invention, the overlapping descriptions therebetween are omitted to avoid excessive complication of the specification due to repetitive descriptions thereof.

The foregoing kit contains antibodies, and thus can be manufactured suitable for various immunoassay or immunostaining methods. The immunoassay or immunostaining methods include, but are not limited to, radioactive immunoassay, radioactive immunoprecipitation, immunoprecipitation, enzyme-linked immunosorbent assay (ELISA), capture-ELISA, inhibition or competition analysis, sandwich assay, flow cytometry, immunofluorescence, and immunoaffinity purification. The immunoassay or immunostaining methods are disclosed in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, the contents of which are incorporated herein by reference.

For example, when the method of the present invention is performed according to the radioimmunoassay method, an antibody labeled with a radioactive isotope (e.g., C14, I125, P32, and S35) can be used to detect an HER2 protein. When the method of the present invention is performed according to the ELISA method, a particular embodiment of the present invention includes the steps of: (i) coating a surface of a solid substrate with a sample to be analyzed; (ii) incubating an antibody to HER2 as primary antibody and the sample; (iii) incubating the product in step (ii) and a secondary antibody conjugated to an enzyme; and (iv) determining the activity of the enzyme.

A suitable example of the solid substrate is a hydrocarbon polymer (e.g., polystyrene and polypropylene), glass, a metal, or a gel, and most specifically a microtiter plate.

The enzyme conjugated to the secondary antibody includes, but is not limited to, enzymes that catalyze a chromogenic reaction, a fluorescent reaction, a luminescent reaction, or an infrared reaction, and includes for examples alkaline phosphatase, β-galactosidase, horseradish peroxidase, luciferase, and cytochrome $P_{450}$. In cases where alkaline phosphatase is used as an enzyme conjugated to the secondary primary, colorimetric reaction substrates may be used such as bromo-chloro-indolyl phosphate (BCIP), nitroblue tetrazolium (NBT), naphthol-AS-B1-phosphate, and enhanced chemifluorescence (ECF); and in cases where horseradish peroxidase is used as an enzyme conjugated to the secondary primary, substrates may be used, such as chloronaphthol, aminoethyl carbazole, diaminobenzidine, D-luciferin, lucigenin (bis-N-methylacridinium nitrate), resorufin benzyl ether, luminol, 10-acetyl-3,7-dihydroxyphenoxazine (Amplex Red reagent), p-phenylenediamine-HCl and pyrocatechol (HYR), tetramethylbenzidine (TMB), 2,2'-Azine-di[3-ethylbenzthiazoline sulfonate] (ABTS), o-phenylenediamine (OPD), and naphthol/pyror, glucose oxidase, t-NBT (nitroblue tetrazolium), and m-PMS (phenazine methosulfate).

In cases where the method of the present invention is performed by capture-ELISA, a particular embodiment of the present invention includes the steps of: (i) coating a surface of a solid substrate with an antibody to HER2 as a capturing antibody; (ii) reacting the capturing antibody with a sample; (iii) reacting the product in step (ii) with a HER2 detecting antibody conjugated to a label generating a signal; and (iv) measuring the signal generated from the label.

The detecting antibody has a label that generates a detectable signal. Examples of the label include, but are not limited to, chemicals (e.g., biotin), enzymes (alkaline phosphatase, β-galactosidase, horse radish peroxidase, and cytochrome $P_{450}$), radioactive substances (e.g., $C^{14}$, $I^{125}$, $P^{32}$, and $S^{35}$), fluorescent substances (e.g., fluorescein), light-emitting substances, chemiluminescent substances, and fluorescence resonance energy transfer (FRET). Various labels and labeling methods are described in Ed Harlow and David Lane, Using Antibodies: A Laboratory Manual, Cold Spring Harbor Laboratory Press, 1999.

In the ELISA method or capture-ELISA method, the measurement of the funeral enzyme activity or the measurement of signals may be carried out according to various methods known in the art. A signal may be easily detected using streptavidin when biotin is used as a label, and a signal may be easily detected using luciferin when luciferase is used as a label.

Examples of the sample applicable to the kit of the present invention include, but are not limited to, cells, tissues or tissue-derived extracts, lysate or purified materials, blood, plasma, serum, lymph, or ascites.

The antibody of the present invention may be used for in vivo or in vitro imaging. According to another aspect of the present invention, the present invention provides a composition for imaging, containing a conjugate in which the antibody of the present invention is conjugated to a label generating a detectable signal conjugated to the antibody.

The label capable of generating a detectable signal includes T1 contrast materials (e.g., Gd chelate compounds), T2 contrast materials (e.g., superparamagnetic materials (e.g., magnetite, $Fe_3O_4$, $\gamma$-$Fe_2O_3$, manganese ferrite, cobalt ferrite, and nickel ferrite)), radioactive isotopes (e.g., $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$, and $^{206}Bi$), fluorescent materials (fluorescein, phycoerythrin, rhodamine, lissamine, and Cy3/Cy5), chemiluminescent materials, magnetic particles, mass labels, and dense electron particles, but are not limited thereto.

Advantageous Effects

Features and advantages of the present invention are summarized as follows.

(a) The present invention leads to an improvement of druggability by substituting an amino acid residue at a particular site of a mother antibody to improve the stability of an antibody.

(b) The modified antibody of the present invention had significantly improved stability while having almost the same productivity and efficacy, compared with the mother antibody hz1E11.

(c) Therefore, the modified antibody of the present invention exhibits excellent characteristics, such as a reduction of production costs, an inhibition of efficacy, and a reduction of side effects, in the development of HER2-specific antibodies.

DETAILED DESCRIPTION

Figure 1:
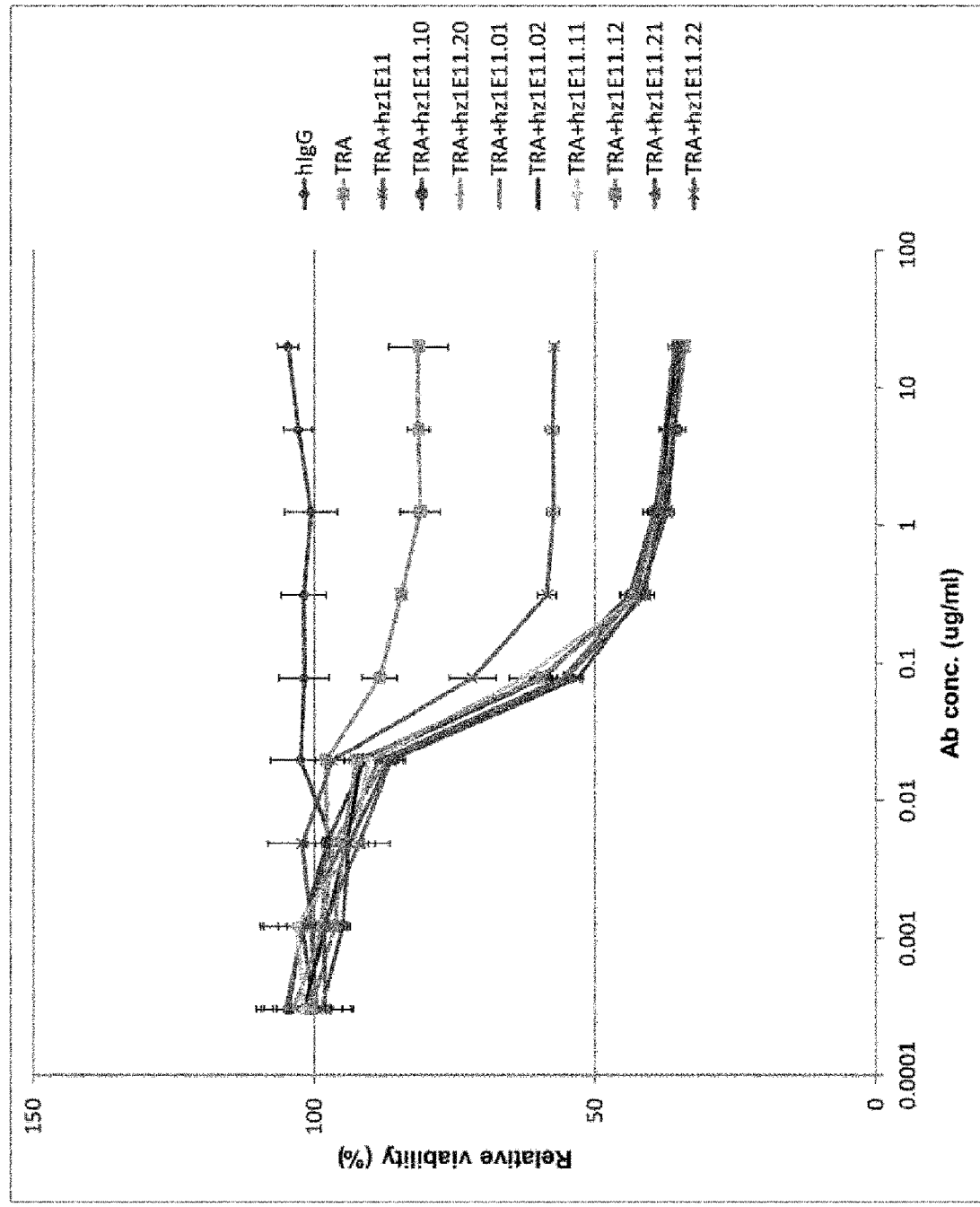
FIG. 1 shows ELISA analysis results as to whether antibodies with improved stability specifically bind to HER2 out of ErbB family proteins (HER1, HER2, HER3, and HER4) to which HER2 belongs. hz15E3, trastuzumab, and AMG-888 (see Li C. et al., Discov Med. 2013 September; 16(87):79-92) were used as control antibodies. In the graph, "Anti-HER2 Ab" represents trastuzumab, "Anti-EGFR Ab" represents hz15E3, and "Anti-HER3 Ab" represents AMG-888. Meanwhile, "2nd only" represents a negative control.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Antibody Modification for Stability Improvement

For the improvement of stability of antibody hz1E11 that has been developed (see Korean Patent No. 1453462), the effect of amino acid residues at various loci on the stability of the antibody was analyzed. Through analysis results, amino acids at four sites of heavy chain and light chain variable regions were identified as sites that could have an effect on stability. The amino acid sequences of the heavy chain and light chain variable regions of the mother antibody hz1E11 are shown in table 1. Asn(N) and Gly(G), corresponding to numbers 52a and 53, according to the Kabat numbering scheme, in the heavy chain region, and Asp(D) and Gly(G), corresponding to numbers 56 and 57, according to the Kabat numbering scheme, in the light chain region, were modified with Ala(A) using overlapping PCR.

The variable regions and constant regions of the heavy chain and light chain were amplified, and these were linked to achieve cloning. The primers used for amplification are shown in Table 2, and PCR at 95° C. for 30 seconds, 57° C. for 30 seconds, and 72° C. for 60 seconds using the above-described primers and GoTaq DNA polymerase (Promega, Cat. No. M3005) was repeated 30 times. The amplified PCR products of the variable and constant regions were electrophoresed on 1% agarose gel, and then purified by using Qiaquick gel extraction kit (QIAGEN, Cat. No. 28706). A gene product was prepared by mixing the PCR product of the variable region and the PCR product of the constant region in the same amount and then conducting overlap extension PCR using a forward primer of the variable region and a reverse primer of the constant region in order to link the variable region and the constant region. The gene product was purified by the same method. The overlap extension PCR at 94° C. for 30 seconds, 57° C. for 30 seconds, and 72° C. for 120 seconds using GoTaq DNA polymerase (Promega, Cat. No. M3005) was repeated 30 times.

For the investigation of an effect of each region on stability, a total of eight types of antibodies from antibodies modified alone to antibodies with two modified amino acid sequences (Table 3).

TABLE 1

| Mother antibody (hz1E11) | Amino acid sequence |
|---|---|
| Heavy chain variable region (SEQ ID NO: 7) | EVQLVESGGGLVQPGGSLRLSCAASGFTFSSYTM SWVRQAPGKGLEWVAYISNGGGSTYYPDTVKGRF TISRDNAKNSLYLQMNSLRAEDTAVYYCARHLGG TASFDYWGQGTLVTVSS |
| Light chain variable region (SEQ ID NO: 8) | DIQMTQSPSSLSASVGDRVTITCLASQTIGTWLA WYQQKPGKAPKLLIYVATSLADGVPSRFSGSGSG TDFTLTISSLQPEDFATYYCQQNAYAPWTFGQGT KVEIK |

TABLE 2

| Primers for amplification of variable regions | |
|---|---|
| Primer name | Sequence |
| F_N52aA | GTAGCCTACATCTCCGCCGGGGCGGAAGTAC (SEQ ID NO: 15) |
| R_N52aA | GTACTTCCGCCCCGGCGGAGATGTAGGCTAC (SEQ ID NO: 16) |
| F_G53A | CTACATCTCCAACGCCGGCGGAAGTACGTA (SEQ ID NO: 17) |
| R_G53A | TACGTACTTCCGCCGGCGTTGGAGATGTAG (SEQ ID NO: 18) |
| F_D56A | GCAACGAGTCTCGCTGCCGGTGTGCCTTCCAGA (SEQ ID NO: 19) |
| R_D56A | TCTGGAAGGCACACCGGCAGCGAGACTCGTTGC (SEQ ID NO: 20) |
| F_G57A | CGAGTCTCGCTGACGCCGTGCCTTCCAGATTT (SEQ ID NO: 21) |
| R_G57A | AAATCTGGAAGGCACGGCGTCAGCGAGACTCG (SEQ ID NO: 22) |

TABLE 3

| | Antibody | Locus of modification |
|---|---|---|
| Modified antibody | hz1E11.10 | Heavy chain N52aA |
| | hz1E11.20 | Heavy chain G53A |
| | hz1E11.01 | Light chain D56A |
| | hz1E11.02 | Light chain G57A |
| | hz1E11.11 | Heavy chain N52aA/Light chain D56A |
| | hz1E11.12 | Heavy chain N52aA/Light chain G57A |
| | hz1E11.21 | Heavy chain G53A/Light chain D56A |
| | hz1E11.22 | Heavy chain G53A/Light chain G57A |
| Mother antibody | hz1E11 | — |

Example 2: Confirmation of Productivity of Modified Antibodies

Productivity analysis was carried out to investigate whether the modification for improving stability has an effect on the productivity of the mother antibody hz1E11. Cloning vectors of the modified antibodies in example 1 were constructed by a method disclosed in Korean Patent No. 1453462. The cloned vectors were transiently transfected in FreeStyle™ 293F (Invitrogen, Cat. No. R790-07) animal cells using polyethylene imine (Polyscience Inc., Cat. No. 23966), and then the modified antibodies were purified from cell cultures by using Protein-A Ceramic HyperD F resin (PALL, Cat No. 20078-028). The purified antibodies were quantified by using UV analysis, followed by SDS-PAGE, and then the concentration and purity thereof were investigated through Coomassie blue staining. According to the productivity analysis, it could be confirmed that hz1E11.10 and hz1E11.20, of which only the heavy chain was modified alone, showed better productivity than the mother antibody hz1E11. However, it was confirmed that hz1E11.01 and hz1E11.02, of which only the light chain was modified alone, showed rather worse productivity. The fact that antibodies, of which both the heavy chain and the light chain were modified, show slightly lower productivity than the mother antibody hz1E11 is shown in table 4.

TABLE 4

| Antibody | Culture volume (ml) | Production (μg) | Yield (mg/L) |
| --- | --- | --- | --- |
| hz1E11.10 | 30 | 1.414 | 47.1 |
| hz1E11.20 | 30 | 1.264 | 42.1 |
| hz1E11.01 | 30 | 0.784 | 26.1 |
| hz1E11.02 | 30 | 0.750 | 25.0 |
| hz1E11.11 | 30 | 0.857 | 28.6 |
| hz1E11.12 | 30 | 0.783 | 26.1 |
| hz1E11.21 | 30 | 0.640 | 21.3 |
| hz1E11.22 | 30 | 0.845 | 28.2 |
| hz1E11 | 30 | 0.992 | 33.1 |

Example 3: Development of Antibody to HER2

For the investigation whether or not antibodies to HER2, the antibodies having improved stability, bind to the target HER2, ELISA was used. For ELISA, the extracellular domain (ECD) of ERBB family protein was produced using animal cells, and then used as an antigen. DNA having a form in which a hinge region and Fc region ($CH_2$—$CH_3$) of human IgG1 were bound to the C-terminus of ECD was cloned into pCEP4 vector (Invitrogen, Cat. No. V044-50) by using restriction enzymes HindIII and BamHI. Then, the cloned vectors transiently transfected in FreeStyle™ 293F (Invitrogen, Cat. No. R790-07) animal cells using polyethylene imine (Polyscience Inc., Cat. No. 23966), and then EGFR-ECF Fc, HER2-ECD Fc, and HER3-ECD Fc fusion proteins were purified from the cell culture by using Protein-A Ceramic HyperD F resin (PALL, Cat No. 20078-028). The purified proteins were quantified using Protein assay dye (Bio-Rad, Cat. No. 500-0006), followed by SDS-PAGE, and the concentration and purity thereof were investigated through Coomassie blue staining.

EGFR-ECF-Fc, HER2-ECD-Fc, HER3-ECD-Fc, or ChromPure human IgG (hIgG, Jackson Immunoresearch Lab. Inc., Cat. No. 009-000-003) was immobilized at a concentration of 1 μg/mL in Costar 96-well plates (Corning, Cat. No. 3590) at room temperature for 1 hour. The plates were washed three times with TBS-T (0.05% Triton X-100), and then blocked three times with 300 μl of TBS-T/SM (2% skim milk) at room temperature for 30 minutes. The blocked plates were washed three times, and the antibodies to HER2, the antibodies having improved stability, were added thereto, followed by incubation at 37° C. for 1 hour. After three times of washing, anti-mouse IgG-HRP (Pierce, Cat. No. 31439) as secondary antibody were diluted to 1:5,000 in TBS-T/SM, followed by incubation at 37° C. for 1 hour. After three times of washing, TMB (SurModics, Cat. No. TMBC-1000-01) was added to perform color development at room temperature for 5 minutes, and then 1 N sulfuric acid (DukSan, Cat. No. 254) was added to stop the color development. The absorbance at 450 nm was measured using Victor X3 (PerkinElmer, Cat. No. 2030-0030), and it was investigated whether or not the antibodies specifically bind to HER2-ECD-Fc. As controls for investigating whether or not ELISA was normally implemented, anti-EGFR Ab (hz15E3), anti-HER2 Ab (trastuzumab), and anti-HER3 Ab (AMG-888), which bind to EGFR, were used. It was confirmed that eight types of antibodies modified for stability improvement specifically bind to only HER2 (FIG. 1).

Example 4: Comparison of Cell Growth Inhibiting Efficacy Among Developed Antibodies For the investigation of cell proliferation inhibiting ability of the antibodies modified for stability improvement, cell viability assay was carried out.

Figure 2:
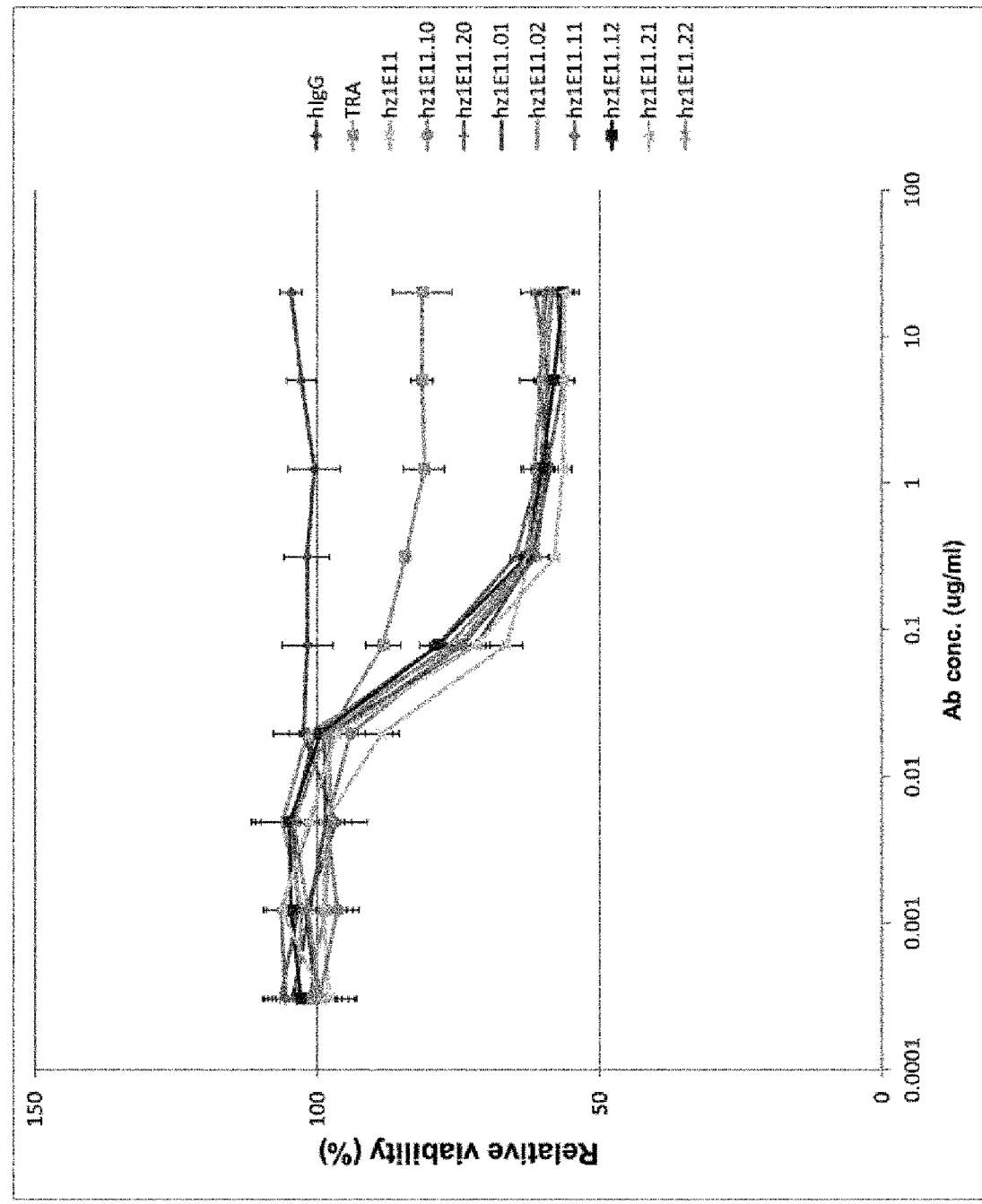
FIG. 2 shows the analysis results of the proportion of cancer cells undergoing apoptosis when NCI-N87 cells were treated with the developed antibodies and trastuzumab alone. In the graph, "hIgG" is human IgG and represents a negative control, and "TRA" represents trastuzumab.
Figure 3:
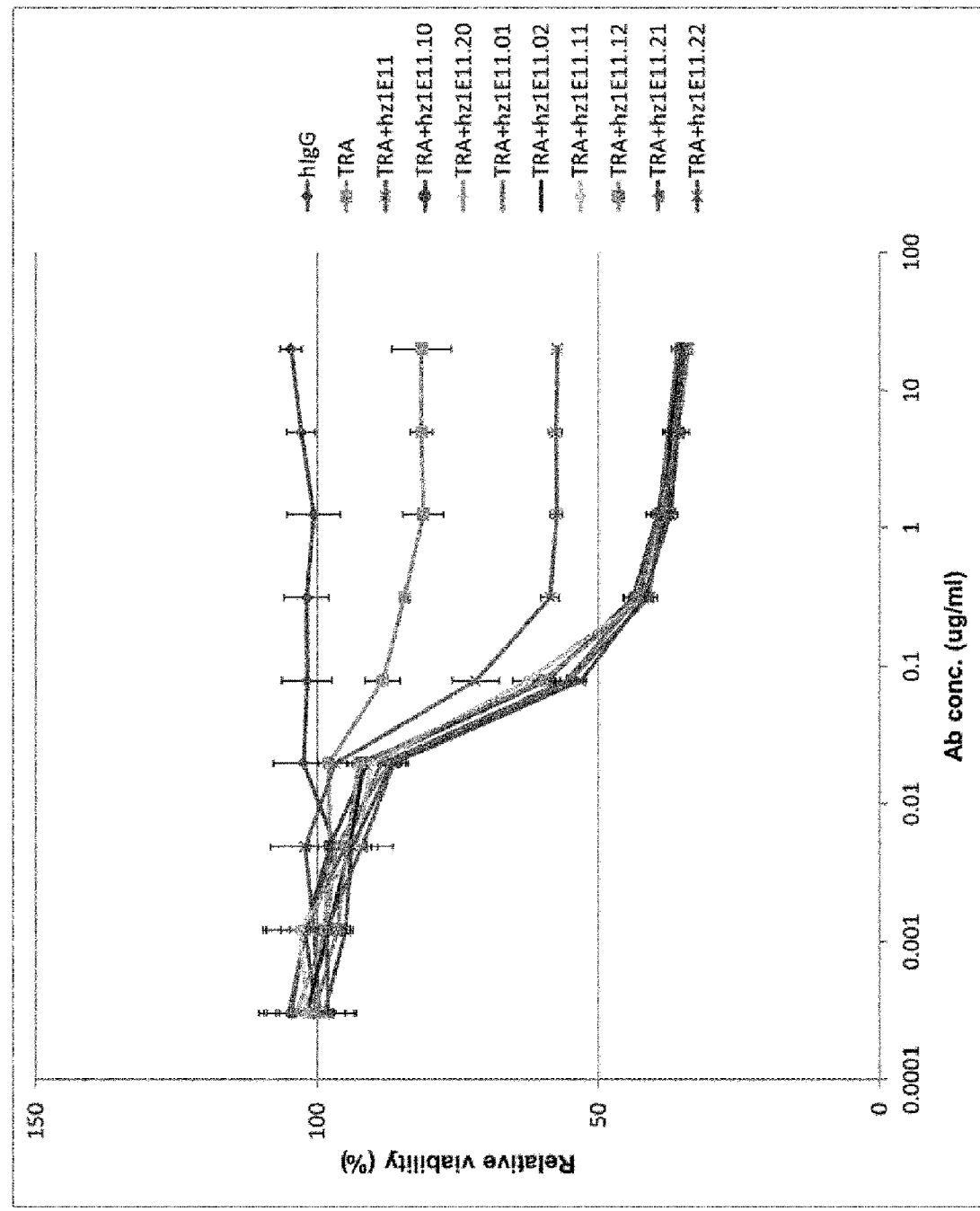
FIG. 3 shows the analysis results of the proportion of cancer cells undergoing apoptosis when NCI-N87 cells were co-treated with the developed antibodies and trastuzumab. In the graph, "hIgG" is human IgG and represents a negative control, and "TRA" represents trastuzumab.

The cell viability assay was carried out by using the antibodies alone or in combination with trastuzumab using NCI-N87 cells corresponding to a representative gastric cancer cell line overexpressing HER2, as a target. For the combinative treatment, the developed antibody and trastuzumab were mixed at a ratio (weight ratio) of 1:1. NCI-N87 (ATCC, Cat No. CRL-5822, 10,000 cells/well) cells were dispensed with a volume of 80 μl in 96-plates and incubated for 24 hours, so that NCI-N87 cells were immobilized in the 96-well plates. The next day, 40 μl of each of the antibodies was added to the cells in culture. The final concentration of each of the antibodies for treatment was at maximum 20 μg/mL, and the assay was carried out at nine concentrations obtained by sequential dilution of 1:4. For combinative treatment with trastuzumab, the developed antibody and trastuzumab were used at a ratio of 1:1 (for instance, in FIG. 3, for a dose of 1 μg/mL, 1 μg/mL TRA and 1 μg/mL the developed antibody were administered). After the treatment with antibody, NCI-N87 cells were further cultured for 4 days, and then CCK-8 was added to a final concentration of 10%, followed by incubation at 37° C. for 3 hours. Thereafter, the absorbance was measured at 450 nm using Victor X-3. The absorbance of cells treated without antibodies was set to 100%, and the relative viability was calculated (FIGS. 2 and 3).

The eight types of antibodies to HER2, the antibodies having improved stability, showed proliferation inhibiting ability on the NCI-N87 cell line responding to trastuzumab. Furthermore, the developed antibodies had excellent cancer cell proliferation inhibiting stability on NCI-N87 cell line through the combinative treatment with trastuzumab, like in the mother antibody hz1E11, compared with trastuzumab alone (FIGS. 2 and 3).

Example 5: Comparison of Storage Buffer-Dependent Stability Between Mother Antibody and Developed Antibodies For the investigation of stability of the developed modified antibodies, the present inventors conducted an accelerated test or stress test on the mother antibody hz1E11 obtained from CHO cells and the modified antibodies hz1E11.10 and hz1E11.11.

Each type of antibodies was stored in the PBS buffer (137 mM Sodium chloride, 2.7 mM potassium chloride, 4.3 mM sodium phosphate, 1.4 mM potassium, pH 7.4) or a histidine buffer (10 mM Histidine, 150 mM Sodium chloride, pH 6.0) according to the buffer. Each type of antibodies stored in each of the buffers was dispensed at 200 uL in a vial for HPLC (Agilent, Cat No. 5188-6591), which was then capped with a blue screw cap (Agilent, Cat No. 5182-0717), thereby preparing each sample.

Size exclusion chromatography (SEC) samples were prepared with a concentration of 1 mg/mL, and cation-exchange chromatography (CEX) samples were prepared with a concentration of 10 mg/mL.

The prepared samples were stored at temperature/humidity conditions of 4±3° C., 25±3° C. (humidity: 60±5%), and 40±3° C. (humidity: 75±5%) using a thermohygrostat (Jeio Tech, Cat No. TH-DG-150) and a refrigerator (Jeio Tech, Cat No. CLG-150S), and each sample was analyzed for stability 0 and 4 weeks from the time of storage. The samples were analyzed using an Agilent 1260 infinity HPLC instrument. For size-exclusion chromatography, the stability depending on the condition was investigated by confirming the proportion of monomers, and for cation-exchange chromatography, the stability was investigated by confirming the proportion of main peaks.

Specifically, for the analysis of the proportion of monomers, 50 μL of each type of antibody proteins was injected into a TSK-gel G3000SWXL (7.8×300 mm) HPLC column (TOSOH, Part No. 8541) under the condition of a 100 mM sodium phosphate (pH 6.8) (Monobasic, Fluka, Cat No. 17844; Dibasic, Fluka, Cat No 71633) solution mobile phase, and then while the antibody proteins were allowed to flow at a rate of 0.8 mL/min for 20 minutes, protein peaks were detected at UV 280 nm. Protein aggregates were eluted from the column prior to the main peaks, and the purity of the monomers was calculated by comparing the peak areas of the aggregates with the areas of the main peaks.

For the analysis of the proportion of main peaks, proteins were diluted in a 10 mM sodium phosphate (pH 7.0) (Monobasic, Fluka, Cat No. 17844; Dibasic, Fluka, Cat No. 71633) buffer to 1 mg/mL, and 20 μL was injected into a Bio Mab (NP10, PK, 4.6×250 mm) HPLC column (Agilent, Cat No. 5190-2415), and then while a 10 mM sodium phosphate (pH 7.0)(Monobasic, Fluka, Cat No. 17844; Dibasic, Fluka, Cat No. 71633), 1M Sodium chloride (GENERAY, Cat No. 0241) buffer, with a concentration gradient of 0-10%, was allowed to flow at 1 mL/min for 40 minutes, protein peaks were detected at UV 280 nm.

The antibody stability analysis results in the PBS-composition buffer through size-exclusion chromatography and cation-exchange chromatography are shown in Tables 5 and 6.

Also, the antibody stability analysis results in the histidine-composition buffer through size-exclusion chromatography and cation-exchange chromatography are shown in Tables 7 and 8.

TABLE 5

| Antibody | Temperature | Week 0 (monomer; %) | Week 4 (monomer; %) | Week 12 (monomer; %) |
|---|---|---|---|---|
| hz1E11 (PBS) | 4° C. | 97.8 | 99.0 | 98.2 |
| | 25° C. | | 98.6 | 97.8 |
| | 40° C. | | 96.7 | 95.4 |

TABLE 5-continued

| Antibody | Temperature | Week 0 (monomer; %) | Week 4 (monomer; %) | Week 12 (monomer; %) |
|---|---|---|---|---|
| hz1E11.10 (PBS) | 4° C. | 99.0 | 99.4 | 98.7 |
| | 25° C. | | 98.4 | 98.5 |
| | 40° C. | | 97.7 | 96.7 |
| hz1E11.11 (PBS) | 4° C. | 98.5 | 99.4 | 98.2 |
| | 25° C. | | 98.0 | 97.6 |
| | 40° C. | | 96.9 | 95.0 |

TABLE 6

| Antibody | Temperature | Week 0 (main peak; %) | Week 4 (main peak; %) | Week 12 (main peak; %) |
|---|---|---|---|---|
| hz1E11 (PBS) | 4° C. | 62.8 | 60.3 | 62.9 |
| | 25° C. | | 45.3 | 29.9 |
| | 40° C. | | 4.8 | 0.0 |
| hz1E11.10 (PBS) | 4° C. | 77.4 | 80.4 | 66.9 |
| | 25° C. | | 63.0 | 42.6 |
| | 40° C. | | 38.5 | 0.0 |
| hz1E11.11 (PBS) | 4° C. | 88.1 | 75.7 | 74.0 |
| | 25° C. | | 58.5 | 48.3 |
| | 40° C. | | 27.0 | 0.0 |

TABLE 7

| Antibody | Temperature | Week 0 (monomer; %) | Week 4 (monomer; %) | Week 12 (monomer; %) |
|---|---|---|---|---|
| hz1E11 (His) | 4° C. | 98.0 | 99.2 | 98.1 |
| | 25° C. | | 99.0 | 98.3 |
| | 40° C. | | 97.3 | 97.0 |
| hz1E11.10 (His) | 4° C. | 99.3 | 99.7 | 99.0 |
| | 25° C. | | 98.4 | 99.3 |
| | 40° C. | | 98.2 | 98.2 |
| hz1E11.11 (His) | 4° C. | 99.0 | 100.0 | 98.6 |
| | 25° C. | | 98.1 | 98.7 |
| | 40° C. | | 98.0 | 97.9 |

TABLE 8

| Antibody | Temperature | Week 0 (main peak; %) | Week 4 (main peak; %) | Week 12 (main peak; %) |
|---|---|---|---|---|
| hz1E11 (His) | 4° C. | 61.5 | 61.5 | 56.0 |
| | 25° C. | | 61.3 | 56.2 |
| | 40° C. | | 52.8 | 29.3 |
| hz1E11.10 (His) | 4° C. | 78.8 | 70.7 | 81.7 |
| | 25° C. | | 69.1 | 69.2 |
| | 40° C. | | 62.0 | 46.6 |
| hz1E11.11 (His) | 4° C. | 72.2 | 76.9 | 76.4 |
| | 25° C. | | 69.1 | 69.0 |
| | 40° C. | | 65.1 | 49.1 |

The SEC analysis results confirmed that all of the three types of antibodies had 95% or more of monomers, and the CEX analysis results confirmed that the modified antibodies of the present invention, hz1E11.10 and hz1E11.11, had a higher content of main ingredients than the mother antibody hz1E11. Especially, it was confirmed that the modified antibodies showed improved stability compared with the mother antibody in the histidine-composition buffer compared with the PBS-composition buffer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A monoclonal antibody or an antigen binding fragment thereof, wherein each of the antibody or antigen binding fragment comprises:
  (a) a heavy chain variable region comprising (i) complementarity determining region (CDR) H1 comprising the amino acid sequence of SEQ ID NO: 1, (ii) CDRH2 comprising the amino acid sequence of SEQ ID NO: 9, and (iii) CDRH3 comprising the amino acid sequence of SEQ ID NO:3; and
  (b) a light chain variable region comprising CDRL1 comprising the amino acid sequence of SEQ ID NO: 4, CDRL2 comprising the amino acid sequence of SEQ ID NO: 5, and CDRL3 comprising the amino acid sequence of SEQ ID NO: 6,
  wherein each of the antibody or antigen binding fragment thereof specifically binds to human epidermal growth factor receptor 2 (HER2), and
  wherein the antibody has improved stability.

2. The monoclonal antibody or antigen binding fragment thereof of claim 1, comprising:
  a heavy chain variable region comprising the amino acid sequence of SEQ ID NO: 7, wherein the 53rd amino acid residue in SEQ ID NO: 7 is substitution modified with Ala; and
  a light chain variable region comprising the amino acid sequence of SEQ ID NO: 8,
  wherein each of the antibody or antigen binding fragment thereof specifically binds to human epidermal growth factor receptor 2 (HER2), and
  wherein the antibody has improved stability.

3. A monoclonal antibody or an antigen binding fragment thereof, wherein each of the antibody or antigen binding fragment comprises:
  (a) a heavy chain variable region comprising (i) complementarity determining region (CDR) H1 comprising the amino acid sequence of SEQ ID NO: 1, (ii) CDRH2 comprising the amino acid sequence of SEQ ID NO: 9 and (iii) CDRH3 comprising the amino acid sequence of SEQ ID NO: 3; and
  (b) a light chain variable region comprising the amino acid sequence of SEQ ID NO: 12 or the amino acid sequence of SEQ ID NO: 13
  wherein each of the antibody or antigen binding fragment thereof specifically binds to human epidermal growth factor receptor 2 (HER2), and
  wherein the antibody has improved stability.

4. The monoclonal antibody or antigen binding fragment thereof of claim 3,
  wherein the heavy chain variable region comprises the amino acid sequence of SEQ ID NO: 7, wherein the 53rd amino acid residue in SEQ ID NO: 7 is substitution modified with Ala; and
  wherein the light chain variable region comprises the amino acid sequence of SEQ ID NO: 12 or SEQ ID NO: 13.

* * * * *